(12) United States Patent
Brady et al.

(10) Patent No.: US 8,241,355 B2
(45) Date of Patent: Aug. 14, 2012

(54) HAPTIC FOR ACCOMMODATING INTRAOCULAR LENS

(75) Inventors: Daniel G. Brady, San Juan Capistrano, CA (US); Henk A. Weeber, Groningen (NL)

(73) Assignee: Abbott Medical Optics Inc., Santa Ana, CA (US)

( * ) Notice: Subject to any disclaimer, the term of this patent is extended or adjusted under 35 U.S.C. 154(b) by 919 days.

(21) Appl. No.: 11/262,385

(22) Filed: Oct. 28, 2005

(65) Prior Publication Data

US 2007/0100444 A1    May 3, 2007

(51) Int. Cl.
*A61F 2/16* (2006.01)
(52) U.S. Cl. .................. 623/6.37; 623/6.38; 623/6.43
(58) Field of Classification Search ............ 623/6.13, 623/6.32–6.55, 6.22, 6.56
See application file for complete search history.

(56) References Cited

U.S. PATENT DOCUMENTS

| | | |
|---|---|---|
| 4,361,913 A | 12/1982 | Streck |
| 4,370,760 A | 2/1983 | Kelman |
| 4,373,218 A | 2/1983 | Schachar |
| 4,442,553 A | 4/1984 | Hessburg |
| 4,512,040 A | 4/1985 | McClure |
| 4,560,383 A | 12/1985 | Leiske |
| 4,562,600 A | 1/1986 | Ginsberg et al. |
| 4,615,701 A | 10/1986 | Woods |
| 4,641,934 A | 2/1987 | Freeman |
| 4,648,878 A | 3/1987 | Kelman |
| 4,731,078 A | 3/1988 | Stoy et al. |
| 4,769,035 A | 9/1988 | Kelman |
| 4,790,847 A | 12/1988 | Woods |
| 4,813,955 A | 3/1989 | Achatz et al. |
| 4,842,601 A | 6/1989 | Smith |
| 4,888,012 A | 12/1989 | Horn et al. |
| 4,892,543 A | 1/1990 | Turley |
| 4,932,966 A | 6/1990 | Christie et al. |
| 4,932,968 A | 6/1990 | Caldwell et al. |
| 4,963,148 A | 10/1990 | Sulc et al. |
| 4,994,082 A | 2/1991 | Richards et al. |

(Continued)

FOREIGN PATENT DOCUMENTS

CH    6816875 A5    5/1993

(Continued)

OTHER PUBLICATIONS

English translation of WO 93/05733 A1.

(Continued)

*Primary Examiner* — David Isabella
*Assistant Examiner* — Leslie Coburn
(74) *Attorney, Agent, or Firm* — Abbott Medical Optics Inc.

(57) ABSTRACT

A haptic is provided for use in an accommodating intraocular lens. The haptic has multiple filaments, each connected to the edge of the optic at one end. Each filament has a shape that conforms to an equatorial region of the capsular bag. The haptic couples the forces exerted by the capsular bag of the eye during accommodation radially to the edge of the optic, produce a diametric expansion or compression of the optic. This diametric motion distorts the optic, producing a change in any or all of the anterior radius, the posterior radius, and the thickness. These changes affect the power of the lens and/or location of the image. The haptic may optionally have a thin membrane joining the filaments at the optic end, and may optionally have a connecting ring that joins the filaments at the end opposite that of the optic.

25 Claims, 3 Drawing Sheets

U.S. PATENT DOCUMENTS

| | | | |
|---|---|---|---|
| 4,994,083 A | 2/1991 | Sulc et al. | |
| 5,047,051 A | 9/1991 | Cumming | |
| 5,152,789 A | 10/1992 | Willis | |
| 5,171,267 A * | 12/1992 | Ratner et al. | 623/6.57 |
| 5,275,623 A * | 1/1994 | Sarfarazi | 623/6.13 |
| 5,476,514 A | 12/1995 | Cumming | |
| 5,489,302 A | 2/1996 | Skottun | |
| 5,496,366 A | 3/1996 | Cumming | |
| 5,607,472 A | 3/1997 | Thompson | |
| 5,628,795 A | 5/1997 | Langerman | |
| 5,674,282 A | 10/1997 | Cumming | |
| 5,728,155 A * | 3/1998 | Anello et al. | 623/6.47 |
| 5,984,962 A | 11/1999 | Anello et al. | |
| 6,013,101 A | 1/2000 | Israel | |
| 6,051,024 A | 4/2000 | Cumming | |
| 6,083,261 A | 7/2000 | Callahan et al. | |
| 6,110,202 A | 8/2000 | Barraquer et al. | |
| 6,117,171 A | 9/2000 | Skottun | |
| 6,120,538 A | 9/2000 | Rizzo, III et al. | |
| 6,197,059 B1 | 3/2001 | Cumming | |
| 6,200,342 B1 | 3/2001 | Tassignon | |
| 6,217,612 B1 | 4/2001 | Woods | |
| 6,241,777 B1 | 6/2001 | Kellan | |
| 6,261,321 B1 | 7/2001 | Kellan | |
| 6,299,641 B1 | 10/2001 | Woods | |
| 6,423,094 B1 | 7/2002 | Sarfarazi | |
| 6,443,985 B1 * | 9/2002 | Woods | 623/6.46 |
| 6,488,708 B2 | 12/2002 | Sarfarazi | |
| 6,517,577 B1 * | 2/2003 | Callahan et al. | 623/6.49 |
| 6,616,692 B1 | 9/2003 | Glick et al. | |
| 6,926,736 B2 | 8/2005 | Peng et al. | |
| 6,930,838 B2 | 8/2005 | Schachar | |
| 7,097,660 B2 | 8/2006 | Portney | |
| 7,150,759 B2 | 12/2006 | Paul et al. | |
| 7,179,292 B2 | 2/2007 | Worst et al. | |
| 7,186,266 B2 * | 3/2007 | Peyman | 623/6.34 |
| 7,220,279 B2 | 5/2007 | Nun | |
| 7,503,938 B2 | 3/2009 | Phillips | |
| 7,815,678 B2 | 10/2010 | Ben Nun | |
| 2001/0044657 A1 | 11/2001 | Kellan | |
| 2002/0045937 A1 | 4/2002 | Sarfarazi | |
| 2002/0116058 A1 | 8/2002 | Zadno-Azizi et al. | |
| 2002/0193876 A1 | 12/2002 | Lang et al. | |
| 2003/0004569 A1 | 1/2003 | Haefliger | |
| 2003/0060881 A1 * | 3/2003 | Glick et al. | 623/6.37 |
| 2003/0130732 A1 * | 7/2003 | Sarfarazi | 623/6.13 |
| 2003/0187504 A1 * | 10/2003 | Weinschenk et al. | 623/6.22 |
| 2004/0015236 A1 | 1/2004 | Sarfarazi | |
| 2004/0039446 A1 * | 2/2004 | McNicholas | 623/6.37 |
| 2004/0082993 A1 | 4/2004 | Woods | |
| 2004/0082994 A1 * | 4/2004 | Woods et al. | 623/6.34 |
| 2004/0082995 A1 | 4/2004 | Woods | |
| 2004/0111153 A1 | 6/2004 | Woods et al. | |
| 2004/0162612 A1 * | 8/2004 | Portney et al. | 623/6.34 |
| 2004/0181279 A1 | 9/2004 | Nun | |
| 2004/0236423 A1 * | 11/2004 | Zhang et al. | 623/6.37 |
| 2005/0018504 A1 | 1/2005 | Marinelli et al. | |
| 2005/0021139 A1 * | 1/2005 | Shadduck | 623/6.35 |
| 2005/0038510 A1 | 2/2005 | Portney et al. | |
| 2005/0113914 A1 * | 5/2005 | Miller et al. | 623/6.34 |
| 2005/0131535 A1 * | 6/2005 | Woods | 623/6.37 |
| 2005/0137703 A1 * | 6/2005 | Chen | 623/6.13 |
| 2006/0100702 A1 * | 5/2006 | Peyman | 623/6.17 |
| 2006/0238702 A1 | 10/2006 | Glick et al. | |
| 2007/0078515 A1 | 4/2007 | Brady | |
| 2007/0106381 A1 | 5/2007 | Blake | |
| 2007/0129798 A1 | 6/2007 | Chawdhary | |
| 2007/0135915 A1 | 6/2007 | Klima | |
| 2007/0213817 A1 | 9/2007 | Esch et al. | |
| 2007/0260309 A1 | 11/2007 | Richardson | |
| 2008/0161914 A1 | 7/2008 | Brady et al. | |
| 2009/0012609 A1 | 1/2009 | Geraghty et al. | |

FOREIGN PATENT DOCUMENTS

| | | |
|---|---|---|
| DE | 201 09 306 U1 | 8/2001 |
| DE | 101 25 829 A1 | 11/2002 |
| EP | 766540 A1 | 4/1997 |
| EP | 766540 B1 | 8/1999 |
| JP | 2126847 | 5/1990 |
| WO | WO0119288 A1 | 3/2001 |
| WO | WO0189816 A1 | 11/2001 |
| WO | WO0219949 A2 | 3/2002 |
| WO | WO 04/000171 A1 | 12/2003 |
| WO | WO2005115278 A1 | 12/2005 |
| WO | WO2006118452 A1 | 11/2006 |

OTHER PUBLICATIONS

U.S. Appl. No. 09/656,661, filed Sep. 7, 2000.
Thornton S., "Accommodation in Pseudophakia," 1991, pp. 159-162.
U.S. Appl. No. 09/721,072, filed Nov. 22, 2000.
European Search Report for Application No. EP11152227, mailed on Oct. 21, 2011, 7 pages.
Extended European Search Report for Application No. EP11152508, mailed on Oct. 25, 2011, 7 pages.
International Preliminary Report on Patentability and Written Opinion for Application No. PCT/US2006/41500, mailed on Apr. 29, 2008, 9 pages.
International Search Report for Application No. PCT/US2006/41500, mailed on Aug. 23, 2007, 5 pages.

* cited by examiner

HAPTIC FOR ACCOMMODATING INTRAOCULAR LENS

BACKGROUND OF THE INVENTION

1. Field of the Invention

The present invention is directed to intraocular lenses, and more particularly to accommodating intraocular lenses.

2. Description of the Related Art

A human eye can suffer diseases that impair a patient's vision. For instance, a cataract may increase the opacity of the lens, causing blindness. To restore the patient's vision, the diseased lens may be surgically removed and replaced with an artificial lens, known as an intraocular lens, or IOL. An IOL may also be used for presbyopic lens exchange.

The simplest IOLs have a single focal length, or, equivalently, a single power. Unlike the eye's natural lens, which can adjust its focal length within a particular range in a process known as accommodation, these single focal length IOLs cannot accommodate. As a result, objects at a particular position away from the eye appear in focus, while objects at an increasing distance away from that position appear increasingly blurred.

An improvement over the single focal length IOLs is an accommodating IOL, which can adjust its power within a particular range. As a result, the patient can clearly focus on objects in a range of distances away from the eye, rather than at a single distance. This ability to accommodate is of tremendous benefit for the patient, and more closely approximates the patient's natural vision than a single focal length IOL.

When the eye focuses on a relatively distant object, the lens power is at the low end of the accommodation range, which may be referred to as the "far" power. When the eye focuses on a relatively close object, the lens power is at the high end of the accommodation range, which may be referred to as the "near" power. The accomomodation range itself is defined as the near power minus the far power. In general, an accommodation range of 4 diopters is considered sufficient for most patients.

The human eye contains a structure known as the capsular bag, which surrounds the natural lens. The capsular bag is transparent, and serves to hold the lens. In the natural eye, accommodation is initiated by a series of zonular fibers, also known as zonules. The zonules are located in a relatively thick band mostly around the equator of the lens, and impart a largely radial force to the capsular bag that can alter the shape and/or the location of the natural lens and thereby change its power.

In a typical surgery in which the natural lens is removed from the eye, the lens material is typically broken up and vacuumed out of the eye, but the capsular bag is left intact. The remaining capsular bag is extremely useful for an accommodating intraocular lens, in that the eye's natural accommodation is initiated at least in part by the zonules through the capsular bag. The capsular bag may be used to house an accommodating IOL, which in turn can change shape and/or shift in some manner to affect the power and/or the axial location of the image.

The IOL has an optic, which refracts light that passes through it and forms an image on the retina, and a haptic, which is a structure that mechanically couples the optic to the capsular bag. During accommodation, the zonules exert a force on the capsular bag, which in turn exerts a force on the optic. The force may be transmitted from the capsular bag directly to the optic, or from the capsular bag through the haptic to the optic.

A desirable optic for an accommodating IOL is one that distorts in response to a squeezing or expanding radial force applied to the equator of the optic (i.e., by pushing or pulling on the edge of the optic, circumferentially around the optic axis). Under the influence of a squeezing force, the optic bulges slightly in the axial direction, producing more steeply curved anterior and/or posterior faces, and producing an increase in the power of the optic. Likewise, an expanding radial force produces a decrease in the optic power by flattening the optic. This change in power is accomplished in a manner similar to that of the natural eye and is well adapted to accommodation. Furthermore, this method of changing the lens power reduces any undesirable pressures exerted on some of the structures in the eye.

One challenge in implementing such an optic is designing a suitable haptic to couple the optic to the capsular bag. The haptic should permit diametric (or, equivalently, radial) motion of the optic by coupling the force exerted by the capsular bag to the edge of the optic, which is generally not available with known haptics.

For instance, consider a haptic disclosed in United States Patent Application Publication No. US 2005/0131535, published Jun. 16, 2005 to Randall Woods. The haptic of Woods is a generally resilient, discoid-shaped body that fits inside the capsular bag. The posterior side of the haptic houses a lens that is typically kept in contact with the posterior wall of the capsular bag. During accommodation, so that the eye can focus on near objects, the capsular bag compresses radially and bulges axially, and the optic, which is held in contact with the posterior wall of the capsular bag, distorts and thereby changes its power.

In Woods, the optic itself is surrounded diametrically by a solid body, referred to by Woods as a "resilient body". Such a resilient body limits the coupling of radial forces to the optic itself. For instance, a compressive radial force exerted by the capsular bag on the haptic would be partially absorbed by the haptic itself, which would couple the compressive force partially into compressing its own material in the region surround the optic. Likewise, an expansive force exerted by the capsular bag on the haptic would also be largely absorbed by the haptic, which would have to stretch in a tangential manner in the region surrounding the optic.

Haptic designs that are used with other IOL styles are generally unsuitable as well. As an example, consider the haptics used in a style of accommodating IOL in which the forces applied by the capsular bag result primarily in an axial translation of the optic, without a significant distortion of the optic. As a specific example, U.S. Pat. No. 5,275,623, issued Jan. 4, 1994 to Faezeh Sarfarazi, discloses a lens that uses a pair of optics and a flexible haptic that responds to the forces of the capsular bag by changing the separation between the optics. Both optics have individual powers, and the total optical power of the eye is adjusted by altering the separation between the optics. The optics themselves are not significantly distorted. Indeed, the haptic largely prevents distortion of the optics by encircling the circumference of the optic with a ring that axially translates the optic under the influence of the capsular bag forces, but retains its own shape under said forces. In general, a haptic in which the optic is encircled by a thick supporting ring is unsuitable, because the forces imparted by the capsular bag are not sufficiently coupled to the edge of the optic.

As yet another example that known haptics are generally unsuitable for coupling the capsular bag forces directly to the diameter of the optic, consider United States Patent Application Publication No. US 2004/0181279, published Sep. 16, 2004 to Yehoshua Nun. Nun discloses a lens that has an optic located between a rigid haptic and the posterior wall of the capsular bag. As the zonules exert force on the capsular bag, the optic is compressed or expanded against the rigid haptic, leading to a change in the radii of the optic as well as the optic thickness. A potential drawback of the Nun IOL is that the haptic is biased anteriorly by pressure from the optic, and may lead to fatigue at the points where the haptic is mounted against the ciliary body in the eye. In addition, distortion of the optic is accomplished by longitudinal (or, equivalently, axial) forces, exerted between the capsular bag wall and the rigid haptic. Indeed, this haptic is also unsuitable for coupling the capsular bag forces to the edge of the optic.

Accordingly, there exists a need for an intraocular lens with a haptic that permits diametric motion of the optic by efficiently coupling the force exerted by the capsular bag and zonules to the edge of the optic. Such a haptic would enable use of a desirable style of optic, which changes its power (i.e., radius of curvature, shape and/or thickness) in response to a squeezing or expanding force applied radially to its edge.

BRIEF SUMMARY OF THE INVENTION

It is an object of the present invention to provide a haptic for use in an accommodating intraocular lens. The haptic couples the forces exerted by the capsular bag of the eye during accommodation to the edge of the optic, preferably radially, producing a diametric expansion or compression of the optic and optionally producing a moment on the optic. This diametric motion distorts the optic, producing a change in any or all of the anterior radius, the posterior radius, and the thickness. Diametric motion may cause axial shift of the optic location in some embodiments as well. These changes affect the power of the lens and/or location of the image.

An embodiment is an intraocular lens for implantation in a capsular bag of an eye, comprising an adjustable optic; and a haptic, the haptic comprising a plurality of filaments, each filament having a first end, a second end opposite the first end, and a coupling portion between the first end and the second end. The first end of each filament extends substantially radially from a peripheral edge of the adjustable optic. The plurality of filaments are unconnected to each other at their first and second ends. The haptic is configured to transmit forces to alter at least one of the shape or the thickness of the adjustable optic.

A further embodiment is an intraocular lens for implantation in a capsular bag of an eye, comprising an adjustable optic; and a haptic, the haptic comprising a plurality of filaments, each filament having a first end, a second end opposite the first end, and a coupling portion between the first end and the second end. The first end of each filament extends substantially radially from a peripheral edge of the adjustable optic. The plurality of filaments are unconnected to each other at their first ends. The coupling portion of each filament has a generally uniform cross-section along its length. The haptic is configured to transmit forces to alter at least one of the shape or the thickness of the adjustable optic.

A further embodiment is a haptic for an intraocular lens for implantation in a capsular bag of an eye, comprising a plurality of filaments, each having a first end extending from a peripheral edge of an adjustable optic to an equatorial region of the capsular bag. The first ends are connected by a membrane. Each filament has a generally uniform cross-section along its length.

A further embodiment is a method of stabilizing an intraocular lens comprising an optic and a haptic, the haptic comprising a plurality of filaments, each filament having a proximal end extending from a peripheral edge of the optic and a distal end distant from the proximal end, the method comprising forming a ring which is parallel to the peripheral edge of the optic and is axially separated from the peripheral edge of the optic; and joining the filaments at their distal ends to the ring. The haptic stabilizes the positions of the filaments relative to each other.

DETAILED DESCRIPTION OF THE INVENTION

In a healthy human eye, the natural lens is housed in a structure known as the capsular bag. The capsular bag is driven by zonular fibers (also known as zonules) in the eye, which can compress and/or pull on the capsular bag to change its shape. The motions of the capsular bag distort the natural lens in order to change its power and/or the location of the image, so that the eye can focus on objects at varying distances away from the eye in a process known as accommodation.

For some people suffering from cataracts, the natural lens of the eye becomes clouded or opaque. If left untreated, the vision of the eye becomes degraded and blindness can occur in the eye. A standard treatment is surgery, during which the natural lens is broken up, removed, and replaced with a manufactured intraocular lens. Typically, the capsular bag is left intact in the eye, so that it may house the implanted intraocular lens.

Because the capsular bag is capable of motion, initiated by the zonules, it is desirable that the implanted intraocular lens change its power and/or the location of the image in a manner similar to that of the natural lens. Such an accommodating lens may produce vastly improved vision over a lens with a fixed power and location that does not accommodate.

Figure 1:
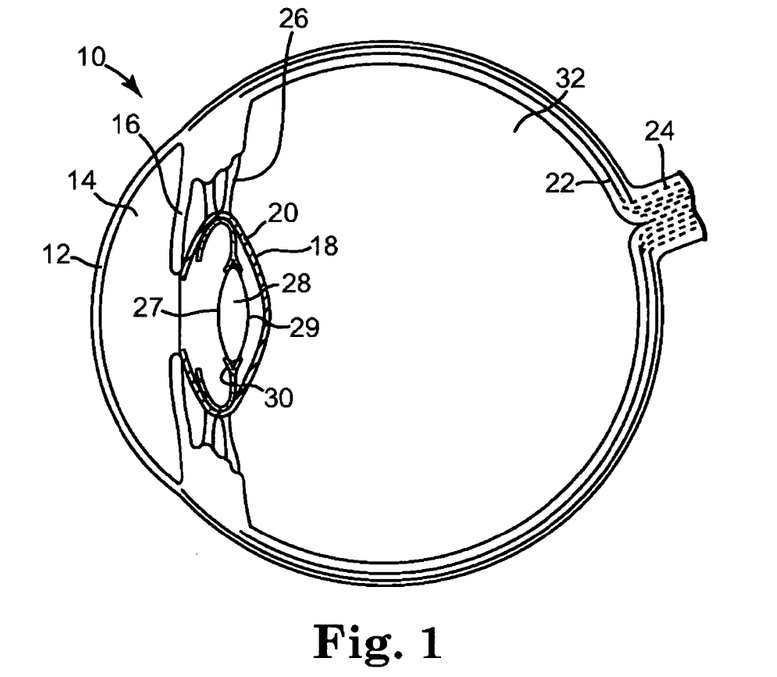
FIG. 1 is a plan drawing of a human eye having an implanted intraocular lens, in an accommodative "near" state.

FIG. 1 shows a human eye 10, after an accommodating intraocular lens according to embodiments of the present invention has been implanted. Light enters from the left of FIG. 1, and passes through the cornea 12, the anterior chamber 14, the iris 16, and enters the capsular bag 18. Prior to surgery, the natural lens occupied essentially the entire interior of the capsular bag 18. After surgery, the capsular bag 18 houses the intraocular lens, in addition to a fluid that occupies the remaining volume and equalizes the pressure in the eye. The intraocular lens is described in more detail below. After passing through the intraocular lens, light exits the posterior wall 20 of the capsular bag 18, passes through the posterior chamber 32, and strikes the retina 22, which detects the light and converts it to a signal transmitted through the optic nerve 24 to the brain.

A well-corrected eye forms an image at the retina 22. If the lens has too much or too little power, the image shifts axially along the optical axis away from the retina, toward or away from the lens. Note that the power required to focus on a close or near object is more than the power required to focus on a distant or far object. The difference between the "near" and "far" powers is known typically as the range of accommodation. A normal range of accommodation is about 4 diopters, which is considered sufficient for most patients, although as low as 1 or 2 diopters may be acceptable, and in some instances between about 4 diopters and about 10 diopters or more may be useful. Embodiments of the present invention may produce accommodation within this entire range, or as low as 1 diopter, with a preferable range of accommodation between about 2 diopters and about 6 diopters, and more preferably about 4 diopters (for example, 3-5 diopters, 3.5-4.5 diopters, and so forth) of accommodation under normal zonular forces.

The capsular bag is acted upon by the zonules 26, which distort the capsular bag 18 by compressing and/or stretching it radially in a relatively thick band about its equator. Experimentally, it is found that the zonules typically exert a total force of up to about 10 grams of force, often in the range of between about 6 and about 9 grams of force, which is distributed typically generally uniformly around the equator of the capsular bag 18. Although the range of zonule force may vary from patient to patient, it should be noted that for each patient, the range of accommodation is limited by the total force that the zonules 26 can exert. Therefore, it is highly desirable that the intraocular lens be configured to vary its power over the full range of accommodation, in response to this limited range of forces exerted by the zonules. In other words, we would like a relatively large change in power for a relatively small driving force.

Because the zonules' force is limited, it is desirable to use a fairly thin lens, compared to the full thickness of the capsular bag. In general, a thin lens can distort more easily than a very thick one, and may therefore convert the zonules force more efficiently into a change in power. In other words, for a relatively thin lens, a lower force is required to cover the full range of accommodation.

Note that there is an optimum thickness for the lens, which depends on the diameter of the optic. If the lens is thinner than this optimum thickness, the axial stiffness becomes too high and the lens changes power less efficiently. In other words, if the edge thickness is decreased below its optimal value, the amount of diopter power change for a given force is decreased. For instance, for an optic having a diameter of 4.5 mm, an ideal edge thickness may be about 1.9 mm, with edge thicknesses between about 1.4 mm and about 2.4 having acceptable performance as well. Alternately, optic diameters may be in a range between about 4 mm and about 8 mm, and edge thicknesses may be in a range above about 0.2 mm.

Note that the lens may be designed so that its relaxed state is the "far" condition (sometimes referred to as "disaccommodative biased"), the "near" condition ("accommodative biased"), or some condition in between the two ("intermediate biased").

The intraocular lens itself has two components: an optic 28, which is made of a transparent, deformable and/or elastic material, and a haptic 30, which holds the optic 28 in place and mechanically transfers forces on the capsular bag 18 to the optic 28. The haptic 30 may have an engagement member with a central recess that is sized to receive the peripheral edge of the optic 28.

When the eye 10 is focused on a relatively close object, as shown in FIG. 1, the zonules 26 compress the capsular bag 18 in a relatively thick band about its equator. The capsular bag 18 changes shape, becoming thicker at its center and having more steeply curved sides. As a result of this action, the power of the lens increases (i.e., one or both of the radii of curvature can decrease, and/or the lens can become thicker, and/or the lens may also move axially), placing the image of the relatively close object at the retina 22. Note that if the lens could not accommodate, the image of the relatively close object would be located behind the retina, and would appear blurred.

Figure 2:
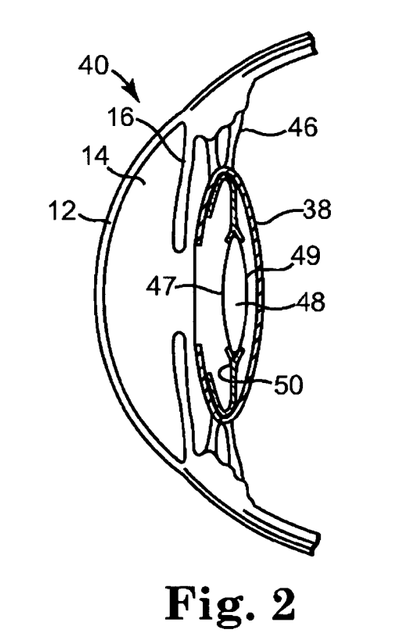
FIG. 2 is a plan drawing of the human eye of FIG. 1, in an accommodative "far" state.

FIG. 2 shows a portion of an eye 40 that is focused on a relatively distant object. The cornea 12 and anterior chamber 14 are typically unaffected by accommodation, and are identical to the corresponding elements in FIG. 1. To focus on the distant object, the zonules 46 retract and change the shape of the capsular bag 38, which becomes thinner at its center and has less steeply curved sides. This reduces the lens power by flattening (i.e., lengthening radii of curvature and/or thinning) the lens, placing the image of the relatively distant object at the retina (not shown).

For embodiments of the present invention as depicted for both the "near" case of FIG. 1 and the "far" case of FIG. 2, the intraocular lens itself deforms and changes in response to the distortion of the capsular bag. For the "near" object, the haptic 30 compresses the optic 28 at its edge, increasing the thickness of the optic 28 at its center and more steeply curving its anterior face 27 and/or its posterior face 29. As a result, the lens power increases. For the "far" object, the haptic 50 expands, pulling on the optic 48 at its edge, and thereby decreasing the thickness of the optic 48 at its center and less steeply curving (e.g., lengthening one or both radius of curvature) its anterior face 47 and/or its posterior face 49. As a result, the lens power decreases.

Note that the specific degrees of change in curvature of the anterior and posterior faces depend on the nominal curvatures. Although the optics 28 and 48 are drawn as bi-convex, they may also be plano-convex, meniscus or other lens shapes. In all of these cases, the optic is compressed or expanded by essentially radial forces exerted primarily at the edge of the optic. In addition, there may be some axial movement of the optic. In some embodiments, the haptic is configured to transfer the generally symmetric radial forces symmetrically to the optic to deform the optic in a spherically symmetric way. However, in alternate embodiments the haptic is configured non-uniformly (e.g., having different material properties, thickness, dimensions, spacing, angles or curvatures), to allow for non-uniform transfer of forces by the haptic to the optic. For example, this could be used to combat astigmatism, coma or other asymmetric aberrations of the eye/lens system. The optics may optionally have one or more diffractive elements, one or more multifocal elements, and/or one or more aspheric elements.

Figure 3:
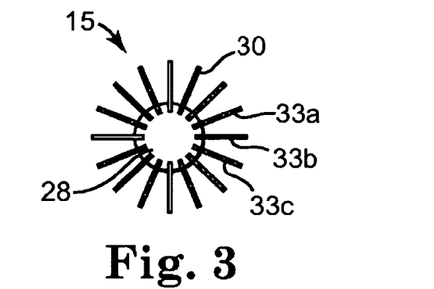
FIG. 3 is an end-on plan drawing of the intraocular lens shown in FIGS. 1 and 2, in an accommodative "near" state.
Figure 4:
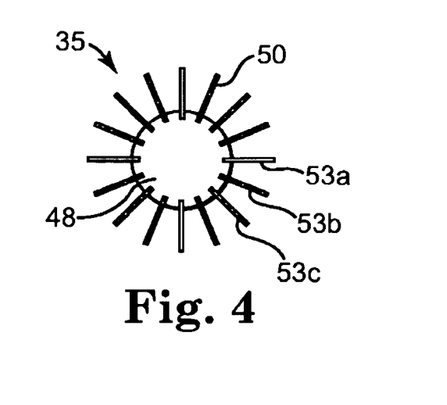
FIG. 4 is an end-on plan drawing of the intraocular lens of FIG. 3, in an accommodative "far" state.

FIGS. 3 and 4 show more explicitly the effects of these radial forces. FIG. 3 shows the intraocular lens 15 of FIG. 1, in an end-on view. The optic 28 is supported by the haptic 30. The intraocular lens 15 is relatively compressed radially, corresponding to the "near" condition of FIG. 1. Similarly, FIG. 4 shows the intraocular lens 35 of FIG. 2 in an end-on view, also with the optic 48 being surrounded by the haptic 50. Here, the intraocular lens 35 is relatively expanded radially, corresponding to the "far" condition of FIG. 2.

Note that each haptic 30 and 50 has several coupling elements 33 and 53. Each coupling element is substantially free to move radially, independently of the other coupling elements. As the capsular bag expands and contracts, the coupling elements transmit the expansion and contraction to the optic itself, causing the optic to expand or contract radially. When the eye views a distant object, the radial forces cause the optic itself to be flatter and thinner than when viewing a close object. In some embodiments, there may also be some axial movement of the optic, which axially translates the image onto the retina and thereby brings it into focus for the eye. Any such axial travel will typically be of secondary importance to the change in power caused by the shape change to the optic caused by the radial forces. The haptic material is preferably stronger or stiffer than the optic material, so that the capsular bag force is largely transmitted to the optic itself, rather than being absorbed by the haptic. Although 16 coupling elements are shown in FIGS. 3 and 4, any suitable number of haptic elements may be used.

Note also that as drawn in FIGS. 1-4, there is no haptic material between adjacent coupling elements. If there were a substantial amount of haptic material between the coupling elements, the radial force would be largely absorbed by the haptic, rather than transmitted to the optic. A helpful analogy may be found in a rubber tire: when the tire is inflated, compressing the outer edge of the tire does not substantially compress the inner hole of the tire, because a large fraction of the compressing force is converted to a tangential compression force at the inner hole. In other words, the radial forces would largely be spent trying to compress or expand the tire material itself in the region surrounding the hole, rather than compressing or expanding the hole itself. In the intraocular lens, if there were significant haptic material between the coupling elements, much of the zonules force would go into compressing or expanding said haptic material, rather than compressing or expanding the optic. This would be a poor use of the limited zonules force, and would introduce inefficiencies into the intraocular lens.

Alternatively, there may be some haptic material between adjacent coupling elements, provided that it is relatively thin if it is made from the same stiff or strong material as the coupling elements. A thin membrane or coating of haptic material between the coupling elements would work adequately, and would not impede any diametric or radial motion of the optic. The membrane could be located symmetrically or asymmetrically along the longitudinal axis of the lens; the haptic may have an even distribution along the longitudinal axis of the optic, or may have more material near the anterior side of the optic, for instance, or may have more material near the posterior side of the optic. Alternately, the membrane may be made in one piece with the coupling elements and may be located anywhere along the coupling elements (i.e. attached to the optic or not so attached, on either end of the coupling elements or somewhere in the middle of the coupling elements). Alternatively, the membrane may be made thicker if it is made from a softer material than that used for the haptic. In general, a thin membrane would function adequately if it is circumferentially compressible, i.e., if its size or circumference can increase or decrease without buckling, warping, or crumpling. For the purposes of this document, the terms circumferentially compressible and circumferentially expandable are taken to mean the same thing.

As a further alternative, the thickness of the material between coupling elements may be increased if said material is weaker or less stiff than the material of the coupling elements themselves. This material may be useful in distributing the haptic force more uniformly around the circumference of the optic. Ultimately, any suitable haptic design may be used, provided that the haptic permits diametric or radial alteration (i.e., change of shape in response to radial or diametric force from the haptic) of the optic in response to the contraction or expansion of the capsular bag.

Note that in FIG. 1, the optic 28 is spatially separated from the posterior wall 20 of the capsular bag 18. In this case, the optic 28 distorts in response to the radial forces applied to its edge by the haptic 30, rather than in response to any longitudinal (or, equivalently, axial) forces applied to the anterior face 27 or posterior face 29. As an alternative, the optic 28 may come into contact with the posterior wall 20 of the capsular bag 18 during part or all of the accommodation range, and in doing so, may receive some longitudinal forces applied to its posterior face 29.

In FIG. 1, the haptic 30 interacts with thin portions of the optic near the edge of the anterior face 27 and the posterior face 29 of the optic. For the purposes of this document, these interactions may be considered to be with the edge of the optic if the forces exerted by the haptic on the optic are essentially radial in nature, and if the thin portions are outside the clear aperture of the optic. Note that in FIGS. 1 and 2, the entire edge of the optic, from anterior to posterior, is contacted by the haptic. Note also that for the purposes of this document, the edge of the optic is intended to mean the peripheral edge of the optic, which is the outermost edge of the optic that connects the anterior and posterior faces of the optic. The edge may be a surface periphery as well.

Figure 5:
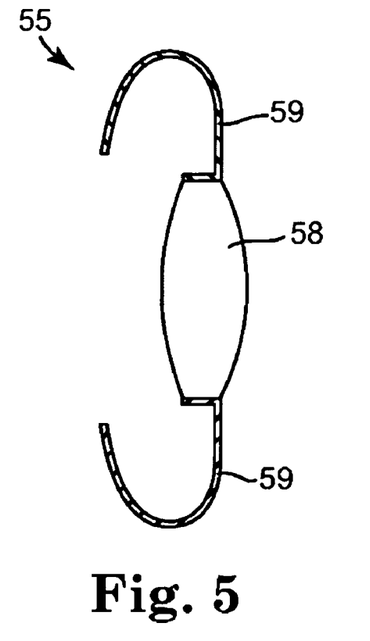
FIG. 5 is a cross-sectional drawing of an intraocular lens.

FIG. 5 shows an alternate embodiment of an intraocular lens 55. The lens has an optic 58, which is mechanically coupled to the capsular bag by a haptic 59. Alternately, the haptic may actually be connected to the capsular bag by fibrosis or surface treatments. As with the embodiments of FIGS. 1-4, the haptic 59 may have several coupling elements or filaments, each of which couples the capsular bag radial force into the optic 58 itself. As a result, the haptic permits diametric expansion and contraction of the optic 58.

Unlike the embodiments of FIGS. 1-4, in which the haptic has an engagement member with a central recess that receives the peripheral edge of the optic, the haptic 59 of FIG. 5 has a planar member that interacts only with the edge of the optic 58. Note that the haptic 59 extends from substantially the entire edge of the optic 58. It will be understood by one of ordinary skill in the art that various other configurations may be used to form an interaction between the haptic and substantially the entire edge of the optic, in addition to the embodiment shown in FIG. 5. Alternatively, the haptic could extend over only a portion (either axially or circumferentially) of the edge of the optic, having asymmetries, discontinuities, and/or a bias toward one side or the other.

Note that the haptic may optionally convert the capsular bag force to a radial torque, rather than transmit the force itself to the optic. In the embodiments of FIGS. 1-5, the equator of the optic may be axially separated from the region at which the capsular bag force is applied, thereby generating a torque. Such a torque affects the optic by changing its shape and/or axially translating the optic.

Figure 6:
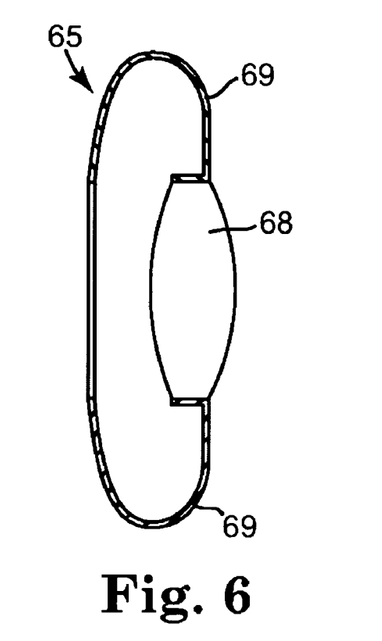
FIG. 6 is a cross-sectional drawing of another embodiment of an intraocular lens.
Figure 7:
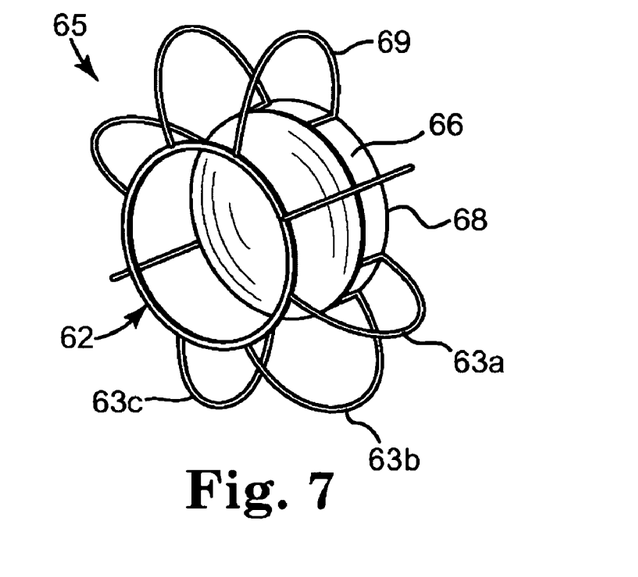
FIG. 7 is a perspective drawing of the intraocular lens of FIG. 6.

A further embodiment of an intraocular lens 65 is shown in FIGS. 6 and 7. In contrast with the haptic 59 of FIG. 5, the coupling elements in FIG. 6 may all be connected on the anterior side of the haptic 69. Because it is undesirable to block the clear aperture of the optic, the anterior side of the haptic may join the coupling elements in a ring 62 surrounding the clear aperture.

Note that in the intraocular lens 65 of FIGS. 6 and 7, a fairly rigid ring 62 joining the coupling elements is acceptable, because it does not surround the optic 68 and it does not impede any radial or diametric motion of the optic. Here, the capsular bag radial force is still directed into radially compressing or expanding the optic 68, only now it does it through a lever arm, with the fixed point on the lever being the anterior ring that joins the coupling elements. Alternately, the coupling elements may connected by a broken ring that connects only some of the coupling elements.

FIG. 7 shows the haptic 69 connected to the optic 68, with an optional membrane 66 between the coupling elements 63. The membrane 66 may be connected to the optic 68 everywhere between the coupling elements 63, or may be connected only in portions, or may be not connected at all in the regions between the coupling elements 63. The membrane 66 may optionally be located between the coupling elements 63 and the optic 68 at each element's connection point, or may be located in only the regions between adjacent coupling elements 63. The membrane may be made as a single piece with the haptic or as a separate element. The membrane 66 may be made of the same material as the haptic 69, with a small enough thickness so that it does not impede any radial expansion or compression of the optic 68 during accommodation. Alternatively, the membrane 66 may be made of a different (typically softer) material than the haptic 69. All of these embodiments could be applied equally to an embodiment as shown in FIG. 5 that does not have the ring 62.

Figure 8:
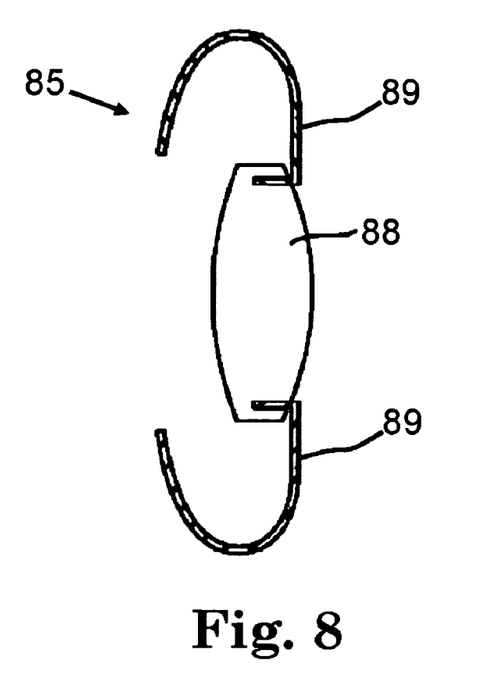
FIG. 8 is a cross-sectional drawing of another embodiment of an intraocular lens.

FIG. 8 shows an intraocular lens 85 in which a haptic 89 connects to an optic 88 by staking through the edge of the optic 88. Note that the axial portion of the coupling elements may be surrounded by the optic material, rather than contacting at only an edge. Contact in this manner may be considered at an edge for the purposes of this document.

In the embodiments of FIGS. 1-8, the optic is preferably oriented on the posterior side of the capsular bag. The preference for a posterior optic is based on a number of factors, including, for example: avoidance or limitation of retinal detachment, which is often more likely with anterior optics; avoidance of iris or anterior chamber complications; and prevention or limitation of posterior capsule opacification. Alternatively, the optic may be oriented on the anterior side of the capsular bag, with the optional connecting ring located on the posterior side of the haptic.

As a further alternative, two optics may be used, with one on the anterior side and one on the posterior side of the haptic. As the capsular bag expands or contracts, the haptic expands or contracts both optics simultaneously. If one optic is stiffer than the other, it could act effectively as the fixed point on a lever arm, similar to the ring 62 in FIG. 7. Optionally, the separation between the two optics may vary as well.

It is instructive to discuss the properties of some suitable materials for the haptic and the optic. In general, the optic should be a fairly soft material, so that it can deform sufficiently under the limited force of the zonules. In general, the haptic should be a fairly hard or stiff material, so that the force from the zonules is transmitted efficiently to the optic. A useful quantity for comparison is the Young's modulus of the materials. For the optic, a low Young's modulus is preferred, such as a value of 28 kpa or less. For the haptic, a high Young's modulus is preferred, such as 1000 kpa or more. Typical haptic materials include, but are not limited to, silicone, acrylic, polyimide, PMMA, polyurethane or other biocompatible materials. Typical optic materials include, but are not limited to, silicone, acrylic, PMMA, and various suitable hydrogels.

The optic itself may be solid throughout, or may be a balloon structure. The optic may be generally soft throughout, or may have a thin, stiff layer on top of a soft structure. The optic may also be a multilayer structure, or may contain multilayered elements.

The haptic may be made integral with the optic. For instance, the two may be molded together. Alternatively, they may be manufactured separately and assembled. Some common assembly methods are silicone glue or adhesive, ultraviolet light-cured adhesive, or heat-cured adhesive.

Note that the haptic is generally a filament in nature, which is a fine or thinly spun thread, fiber, or wire. This filamentary shape minimizes the mass of the haptic. Because the force that can be applied by the capsular bag is limited, and responsiveness to this force is highly desirable, it is also desirable to minimize the mass of the haptic so that the eye can accommodate quickly. A light haptic tends to speed up the response of the eye, which is desirable. The haptic filaments (i.e. coupling elements) have essentially the same size at each point along their length, so that the cross-section of each filament remains essentially uniform along its length. The filaments that form the coupling elements of the various embodiments described above will typically have two ends, one of which is coupled to the optic, with a coupling portion between the two ends for engaging the capsular bag and/or zonules. Note that the connecting ring 62 may optionally have a different thickness than the filaments, and that one or more filaments may have different thicknesses than other filaments. One or more of the filaments may be shaped to produce a bending in a particular manner, as with a pre-bent or a memory-retaining material.

FIGS. 1 to 8 show coupling elements that are generally contained in a plane perpendicular to the edge of the optic. This shape transmits the radial forces exerted by the capsular bag efficiently, without the introduction of any unnecessary torsions, twists, or torques that might arise from a less symmetric shape for the coupling elements. These unnecessary torques would drain energy away from radial compression or expansion of the optic, and would reduce the efficiency of the intraocular lens accommodation. It is understood that other suitable shapes and orientations of the coupling elements may be used.

In contrast with the haptic 59 of FIG. 5, the coupling elements in FIG. 6 may all be connected on the anterior side of the haptic 69. Because it is undesirable to block the clear aperture of the optic, the anterior side of the haptic may join the coupling elements in a ring 62 surrounding the clear aperture.

Figure 9:
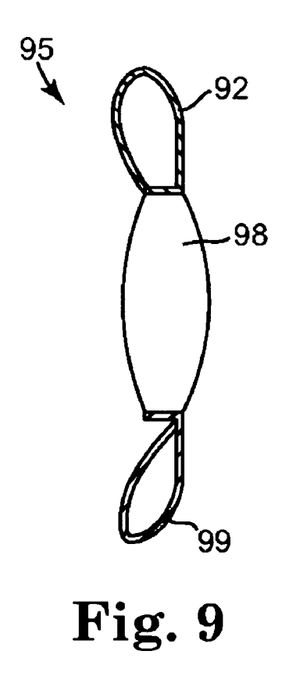
FIG. 9 is a cross-sectional drawing of another embodiment of an intraocular lens.

A further embodiment of an intraocular lens 95 is shown in FIG. 9. The coupling element 92 forms a closed loop, in contrast with many of the haptics in FIGS. 1-8. The coupling element 99 also forms a closed loop, but with a slightly different shape from coupling element 92. Depending on the desired properties of the intraocular lens 95, differently shaped coupling elements may be used around the circumference of optic 98. For instance, having differently shaped coupling elements distributed asymmetrically around the circumference may help generate a deliberate amount of astigmatism during accommodation, which may in turn correct for some astigmatism present in the other components of the eye.

Figure 10:
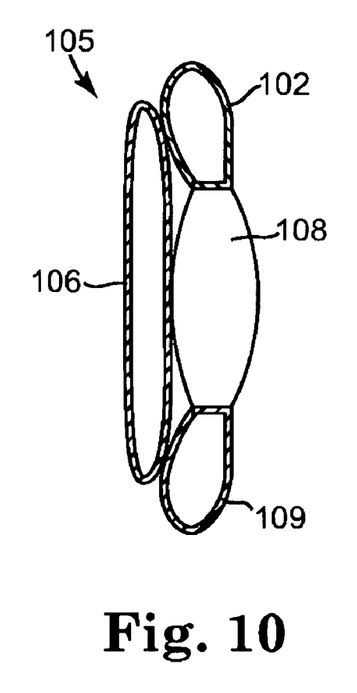
FIG. 10 is a cross-sectional drawing of another embodiment of an intraocular lens.

A further embodiment of an intraocular lens 105 is shown in FIG. 10. An optic 108 is supported by various coupling elements 102 and 109, which are connected by a connecting ring 106. As with the connecting ring 62, the connecting ring 106 does not block the clear aperture of the optic 108, and help stabilize the respective positions of the coupling elements 102 and 109.

Note that as used in this document, the term "radial" is intended to signify that there is neither a longitudinal (or, equivalently, axial) nor a tangential component.

The description of the invention and its applications as set forth herein is illustrative and is not intended to limit the scope of the invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

We claim:

1. An intraocular lens for providing a range of accommodation powers, comprising:
an adjustable optic having an optical axis and an external peripheral edge that extends from an anterior edge to a posterior edge;
a plurality of coupling elements, each coupling element having a first end that interacts with the peripheral edge of the optic, aligned from approximately the posterior edge of the optic and extending alongside the peripheral edge to an anterior location approximately at the anterior edge of the optic; wherein each first end is aligned along an axis substantially parallel to the optical axis;
wherein the coupling element then extends radially outward from only the anterior location approximately at the anterior edge of the optic;
a second end opposite the first end, the coupling elements including a portion between the first and second ends configured to engage an inner surface of an evacuated capsular bag; wherein the first end of at least one coupling element is spaced apart from circumferentially adjacent coupling elements; and
wherein the coupling elements change the shape of the adjustable optic in response to an ocular force.

2. The intraocular lens of claim 1, wherein the coupling elements are connected by a ring at an end opposite the first ends.

3. The intraocular lens of claim 2, wherein the ring is spaced apart from the optic along the optical axis.

4. The intraocular lens of claim 1, wherein the first ends are connected by a membrane.

5. The intraocular lens of claim 4, wherein the membrane is circumferentially compressible.

6. The intraocular lens of claim 4, wherein the membrane is affixed to the adjustable optic at spaced-apart intervals.

7. The intraocular lens of claim 1, wherein the coupling elements are configured to transmit forces to alter at least one of the shape or the thickness of the adjustable optic.

8. The intraocular lens of claim 1, wherein each coupling element is a thin thread, a fiber, or a wire.

9. The intraocular lens of claim 1, wherein the peripheral edge of the optic has an edge thickness that is about 1.9 mm.

10. The intraocular lens of claim 1, wherein the peripheral edge of the optic has an edge thickness that is between about 1.4 mm and 2.4 mm.

11. The intraocular lens of claim 1, wherein the ocular force is up to about 10 grams of force.

12. An intraocular lens for providing a range of accommodation powers, comprising:
an adjustable optic having an optical axis and an external peripheral edge that extends from an anterior edge to a posterior edge; and
a haptic comprising:
a plurality of filaments, each filament having a first end that interacts with the peripheral edge of the optic, aligned from approximately the posterior edge of the optic and extending alongside the peripheral edge to an anterior location approximately at the anterior edge of the optic; wherein each first end is aligned along an axis substantially parallel to the optical axis;
a second end opposite the first end, and a coupling portion between the first end and the second end configured to engage an inner surface of an evacuated capsular bag;
wherein the filaments extend substantially radially outward from only the anterior location approximately at the anterior edge of the optic;
wherein the first end of each filament is spaced apart from adjacent filaments; and wherein the haptic changes the shape of the adjustable optic in response to an ocular force.

13. The intraocular lens of claim 12, wherein the peripheral edge of the adjustable optic is cylindrical, and wherein the haptic has a planar member at its first ends affixed thereto.

14. The intraocular lens of claim 12, wherein the filaments have a higher Young's modulus than the adjustable optic.

15. The intraocular lens of claim 12, wherein the adjustable optic is biconvex.

16. The intraocular lens of claim 12, wherein the adjustable optic faces the anterior of the capsular bag.

17. The intraocular lens of claim 12, wherein each filament is generally contained in a plane perpendicular to the anterior and posterior edges of the optic, the filaments defining a shape that transmits radial forces without the introduction of any twists of the intraocular lens.

18. The intraocular lens of claim 13, wherein the ocular force is up to about 10 grams of force.

19. The intraocular lens of claim 13, wherein the second ends are connected to each other by a ring spaced apart from the optic along the optical axis.

20. An intraocular lens for providing a range of accommodation powers, comprising:
an adjustable optic having an optical axis and an external peripheral edge that extends from an anterior edge to a posterior edge; and
a haptic comprising:
a plurality of filaments, each filament having a first end that interacts with the peripheral edge of the optic, aligned from approximately the posterior edge of the optic and extending alongside the peripheral edge to an anterior location approximately at the anterior edge of the optic; wherein each first end is aligned along an axis substantially parallel to the optical axis;
a second end opposite the first end, and a coupling portion between the first end and the second end, the coupling portion configured to engage an inner surface of an evacuated capsular bag;
wherein the filaments extend substantially radially from only the anterior location approximately at the anterior edge of the adjustable optic;
wherein the second end of each filament is axially separated from the peripheral edge of the optic; wherein the coupling portion of each filament has a generally uniform cross-section along its length; and
wherein the haptic changes the shape of the adjustable optic in response to an ocular force.

21. The intraocular lens of claim 20, further comprising a ring connecting each of the second ends.

22. The intraocular lens of claim 21, wherein the ring is spaced apart from the optic along the optical axis.

23. The intraocular lens of claim 20, wherein the peripheral edge of the optic has an edge thickness that is about 1.9 mm.

24. The intraocular lens of claim 20, wherein the peripheral edge of the optic has an edge thickness that is between about 1.4 mm and 2.4 mm.

25. The intraocular lens of claim 20, wherein the ocular force is up to about 10 grams of force.

* * * * *